United States Patent [19]

Victor et al.

[11] 4,118,300
[45] Oct. 3, 1978

[54] COULOMETRIC TITRATOR

[75] Inventors: Joe M. Victor; James Dougherty, both of Houston, Tex.

[73] Assignee: Petrolite Corporation, St. Louis, Mo.

[21] Appl. No.: 810,834

[22] Filed: Jun. 28, 1977

[51] Int. Cl.$^2$ ............................................. G01N 27/44
[52] U.S. Cl. ............................... 204/195 T; 204/1 T
[58] Field of Search .......................... 204/1 M, 195 T

[56] References Cited

U.S. PATENT DOCUMENTS

| | | | |
|---|---|---|---|
| 3,131,348 | 4/1964 | Taylor et al. | 204/195 T |
| 3,441,490 | 4/1969 | Johansson | 204/195 T |
| 3,779,886 | 12/1973 | Moen et al. | 204/195 T |
| 4,055,478 | 10/1977 | Wilson | 204/1 M |

Primary Examiner—T. Tung
Attorney, Agent, or Firm—Sidney B. Ring; Hyman F. Glass

[57] ABSTRACT

A coulometric titrator for determining, at high accuracy and without time delay problems, small amounts of a specific ion in a solution by the addition of a reactive ion. A sensor provides a signal voltage representing the logarithm of the specific ion concentration to a differential amplifier which also receives as an input a signal from a reference electrode. The differential amplifier produces an error signal applied to a comparator and referenced therein to a certain reference voltage representing a desirable range of rates of change of the error output voltage. The comparator provides a sensor signal voltage representing the difference between the error signal and reference voltage. This sensor signal voltage is applied to an antilogarithm converter which produces an output signal that is proportional to the antilogarithm of the sensor signal voltage. The output signal is received by a reactive ion (silver metal) source means associated with a current source passing a unidirectional current flow between an inert cathode immersed in the solution and the reactive ion source means as an anode for the introduction of the reactive ion (silver) into the solution. As a result, the signal voltage representing the logarithm of a specific ion concentration changes at a constant rate with time, and the reactive ion addition changes in a logarithmically decreasing amount with time in the sample solution until the stoichiometric end point is approached. The present coulometric titrator incorporates (1) a reversing switch which changes the polarity of the measured cell potential to allow the instrument to perform coulometric titrations which have negative going voltage changes near the equivalence point; and/or (2) a slope adjustment which changes the slope of the anti-logarithmic function which allows practical coulometric titrations of systems where the voltage change with concentration is more or less than 60 mV per decade of concentration such as occur in 2 and 3 electron reactions and other more complicated chemical systems.

9 Claims, 4 Drawing Figures

COULOMETRIC TITRATOR

BACKGROUND OF THE INVENTION

1. Field of the Invention

This invention relates to the field of electrochemistry, and more particularly, it relates to the coulometric analysis of specific ions in an electrolytic solution.

2. Description of the Prior Art

Coulometric analysis for specific ions in an electrolytic solution is a well known and established technique in the field of electrochemistry. The development of automatic functioning coulometric titrators for carrying out these analyses has produced many devices of which examples may be found in U.S. Pat. Nos. 3,275,533, 3,398,064, 3,441,490 and 3,647,668. Known automatic titration devices in the electrochemical field for conducting coulometric analysis depend upon a feedback loop which supplies an error signal establishing some fixed relationship between the addition of the reactive ion and a reference point at which the titration of the specific ion sought is believed to have been completed. Obviously, the feedback loop principle is a time domain function and suffers from compound errors. The electrodes employed in conducting the electrochemical analysis have an appreciable capacitance characteristic. Also, an appreciable time delay is caused by the diffusion of ions in the cell and principally the reactive ions introduced into the solution by the coulometric flow of current into the cell. Thus, the time delay problems make inaccurate and difficult-to-produce results in the coulometric titration of specific ions in an aqueous solution. The operator or an automatic feature must terminate with high accuracy and precision in electrochemical analysis the introduction of the reactive ion so that the ions may properly diffuse and the cell "coast" to what is believed to be the actual endpoint. The time delay problem varies with ion concentration and kind which also compounds the problem. The actual endpoint also changes not only with different types of ion but with different solvent composition.

It will be apparent that the coulometric titration employs sensors for the detection of the specific ion whose output, according to the Nernst equation, is a voltage proportional to the logarithm of the specific ion concentration. Thus, the most important component of the coulometric titration system is the sensor for the specific ion. The sensor has to indicate when a sufficient amount of the reactive ion has been added to completely convert this specific ion being analyzed for into a product effectively combining the specific and reactive ions into an insoluble or otherwise non-reactive salt. The sensor must be sensitive only to the specific ion being analyzed, and also, the reactive ion must combine only with the specific ion subject to analysis. Further, there must be a definite relationship in the chemical reaction between the specific and reactive ions and freedom from any interferences by extraneous ions with the desired reaction.

Obviously, automatic functioning coulometric titrators usually depend on electrochemical sensors whose voltage output is proportional to the logarithm of the concentration of the specific ion subject to analysis. This relationship is well known as the Nernst equation. This equation is a proper definition for the steady state of a solution or one where the ion concentrations are changing at a very slow rate. Mathematically, the equation defines that a certain percentage change in specific ion concentration will cause an incremental change in sensor output voltage that is the same independent of the actual magnitude of the specific ion concentration. Therefore, in the automatic coulometric titrator, the electrochemical sensor can be incorporated in its function as a percentage change indicator relative to the specific ion concentration.

As will be apparent, the addition of the reactive ion to the test solution at a constant rate produces ambiguities in the sensor's logarithmic voltage output. More particularly, the specific ion sensor changes voltage at the most rapid rate when the specific ion concentration is at equivalence since the largest percent change in specific ion concentration occurs at this point of the analysis. Therefore, the maximum sensor voltage change and the maximum rate of percentage change of specific ion concentration is known as the inflection point of the electrochemical analysis. High accuracy can be obtained with a constant rate of reactive ion addition only if the electrochemical analysis is done at very low rates of reactive ion addition so that the dynamic problems relating to the phenomena do not cause large analysis errors, but the time of analysis is very long.

The above dynamic electrochemical analysis problems can be very severe when the specific ion sensor suffers from capacitive or any energy storage characteristics in the electrolytic solution. The capacitance function in a dynamic electrochemical analysis requires that the specific ions must either enter or leave the region of the sensor for the voltage output to change. In the optimum form of the coulometric titrator, the transfer of the specific ions and voltage output change are usually independent of the specific ion concentration in the solution and dependent only on the physical construction of the sensor. However, where the capacitance function is encountered, these relationships are no longer valid and appreciable time delay errors arise in this electrochemical analysis.

Unfortunately, the capacitive function about the sensor electrode produces a time delay that becomes proportionally larger as the concentration of the specific ions approaches equivalence. At equivalence concentration levels of the specific ions, the time delay problem causes the most error in the electrochemical analysis since the sensor fails to indicate by output voltage the endpoint until some extended period of time after the actual endpoint has been passed by the continued addition of the reactive ion.

In an application of Homer M. Wilson, application Ser. No. 643,064, filed Dec. 22, 1975, there is disclosed a coulometric titrator arranged to avoid the problems of the time delay error and capacitance function about the sensor electrode. In said coulometric titrator, the novel improvement in electrochemical analysis is achieved by scaler (non-time domain) circuitry which reduces the rate of reactive ion addition logarithmically throughout the analysis. In the preferred embodiment of said coulometric titrator, the addition of the reactive ion is made proportional to the ratio of the anti-logarithm of the specific ion sensor's voltage output and a certain rate controlling reference voltage. In said coulometric titrator, the factor change in the specific ion concentration remains constant and yields a linear rate of sensor voltage change with time. As a result, any dynamic time delay arising from the characteristics of the sensor in detection of the specific ion concentration will have a rate controlling influence and not an endpoint controlling influence. The linear rate of change of sensor output voltage with time is set by the rate controlling reference voltage. Thus, said Wilson coulometric titrator provides not only high speed titrations of great accuracy, but it employs the linear sensor output voltage change to indicate to the operator that the choice of electrochemical analysis parameters is correct.

Since said Wilson titrator has been designed to provide reactive ion proportional to the amount of specific ion left to titrate and has no capability for any other reactive ion demand, the stopping point occurs when some unexpected reactive ion demand becomes the predominant user of the available reactive ion. Said unexpected reactive ion demand of said Wilson titrator is usually the demand for storage of the reactive ion in solution as free ion. Because the characteristics of ions in solution determine the stopping point, any zero shift in sensor voltage does not change the stopping point, but only changes the rate of speed that the stopping point is approaching. The Wilson titrator thus permits accurate operation and accurate answers even though the sensor voltage signal has unexpectedly or even intentionally been shifted by some d.c. amount. Titrators other than the Wilson titrator at the time of the Wilson invention were very dependent on the use of a stable sensor voltage signal and any unexpected shift in sensor voltage signal was such as would cause considerable error in the answer without the operator being conscious of the problem.

Said Wilson invention provided a coulometric titrator for determining the amount of a specific ion in a sample electrolytic solution by the controlled addition of a reactive ion. Said Wilson titrator includes a reference electrode providing a first signal voltage and a specific ion sensing electrode providing a second signal voltage representing the logarithm of the concentration of the specific ion in the same solution in which these electrodes are immersed. Therein, a differential input amplifier receives these first and second signal voltages as its input and provides in its output an error signal voltage representing the difference between the first and second signal voltages; a reference means provides reference voltage for the specific ion in the solution indicative of a particular rate of change of the second signal voltage while the rate of change of the second signal voltage is constant. In addition, in said Wilson titrator, comparator means receive the error signal and the referenced voltage as inputs and has an output of a sensor signal voltage representing the difference between the error signal and reference voltage, and the sensor signal voltage is applied to an antilogarithm converter means which produces an output signal that is proportional to the antilogarithm of the sensor signal voltage. Furthermore, in Wilson, reactive ion source means receive the output signal and are associated with a current source providing a unidirectional current flow between a cathode and an anode immersed in the same solution (one being inert and the other being the reactive ion means) such that the quantum rate of the reactive ion introduced into the sample solution is proportional to the control signal. As a result, in the Wilson titrator, the second signal voltage changes at a constant rate with time and the reactive ion addition changes in a logarithmically decreasing amount with time in the same solution.

In other embodiments of said Wilson invention, a differentiator means may be employed to receive the error signal voltage and to provide a readout representing the change in the error signal voltage with time, and, when the proper rate controlling reference voltage has been selected, this readout is a steady state signal of between 10 and 60 millivolts per minute. Also, in the Wilson invention, a coulometric means may be employed to monitor the coulombs supplied to the reactive ions source means.

In said Wilson titrator, the current at the generating electrodes is controlled by the sensing electrodes and is given by the relationship $i = i_o$ antilog $[-D(E-E_o)]$, wherein $i_o$ is the referencing current, $E-E_o$ the sensor signal voltage and the constant D controls the slope or rate of application of generating current; a value for D which is suitable for a one electron reaction ($n=1$) will result in an impractically low titration rate where two ($n=2$) and three ($n=3$) electron reactions are involved.

Moreover, in the Wilson titrator, only systems in which the error signal voltage E increases in a positive direction are capable of being titrated.

An object of the present invention is to provide an improvement over the Wilson titrator which enables it to carry out titrations at a practical rate regardless of the number of electrons ($n$) involved in the reaction.

An additional object is to provide an improvement in said Wilson titrator which enables it to be used in systems in which the signal voltage increases in a negative manner as well as those in which it increases in a positive manner.

Other objects of this invention will be apparent hereinafter.

SUMMARY OF THE INVENTION

The present invention provides improvements over said Wilson coulometric titrator including reversing switch means and slope adjusting means. The reversing switch means receives the error signal voltage and provides, as output, such voltage in either the positive and negative sense, depending on the position of the switch. The slope adjusting means enables the operator to adjust the slope of the antilogarithm function to the number of electrons involved in the titration in order to obtain a practical titration rate for such electron number.

DESCRIPTION OF SPECIFIC EMBODIMENTS

Figure 1:
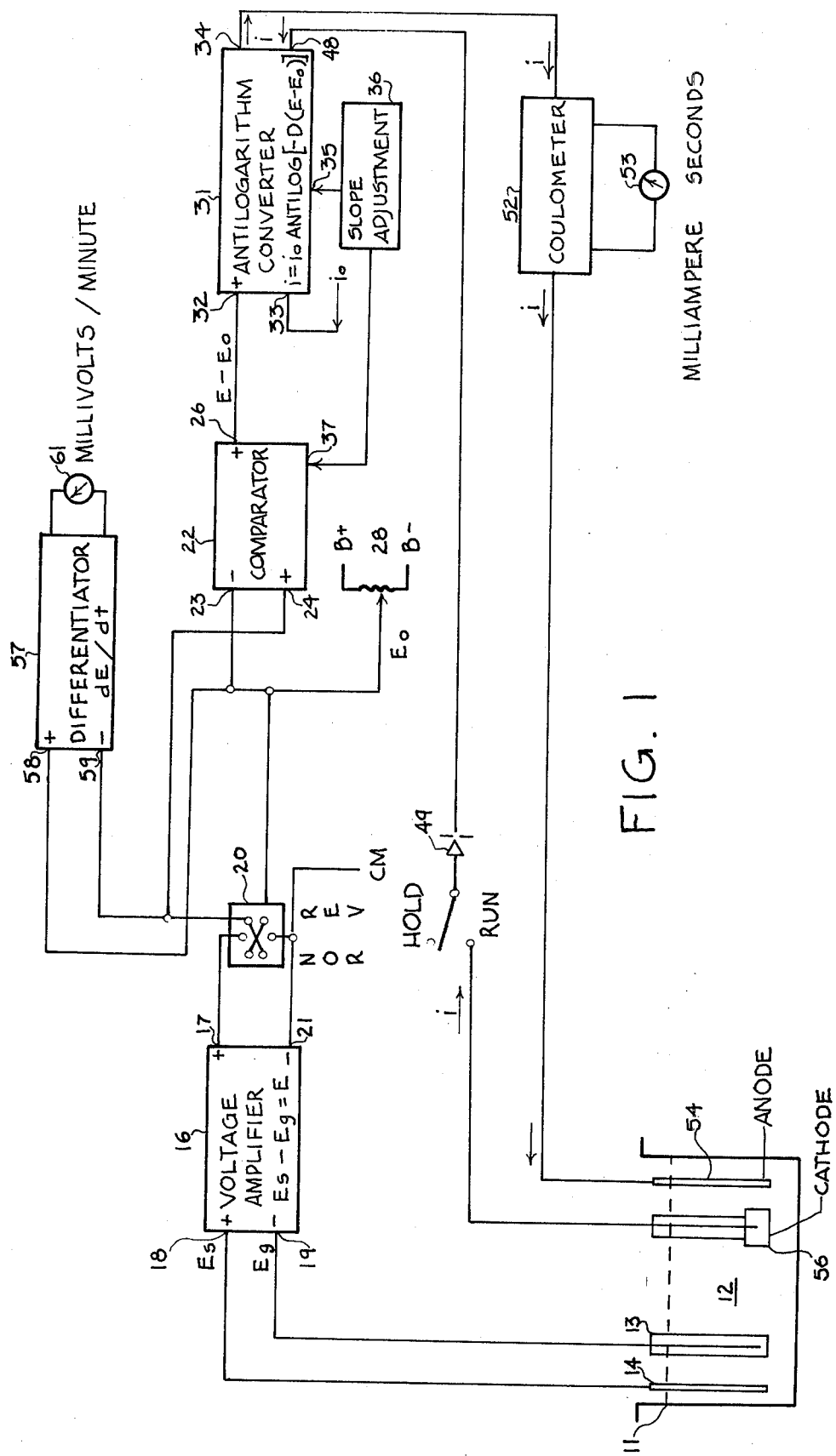
FIG. 1 is an electrical block diagram showing the various elements comprising the coulometric titrator of this invention.

In FIG. 1, there is shown a preferred embodiment of the coulometric titrator of the present invention. The coulometric titrator, as identified by legends, has a plurality of electrical circuit components contained within the various blocks, all components being available in the marketplace or known to the skilled electrochemical analyzer manufacturer.

More particularly, the coulometric titrator employs a cell 11 containing the electrolytic solution incorporating the specific ion to be subjected to electrochemical analysis. The solution 12 is of any suitable volume and preferably is maintained at near ambient or other steady state temperature. Immersed within the solution 12 are a plurality of electrodes associated with the coulometric titrator. These electrodes include a reference electrode 13 to produce a first signal voltage $E_g$ and can be a glass electrode for present descriptive purposes. Closely associated with the reference electrode 13 is a specific ion sensing electrode 14 to produce a second signal voltage $E_s$ representing the logarithm of the amount of the specific ion in the sample solution 12. For example, the specific ion may be the chloride ion, the sulfide ion or the phosphate ion and the electrode 14 can be a silver/silver chloride, silver/silver sulfide, or silver/silver phosphate half cell embodiment, which results in a second signal voltage $E_s$ representing the logarithm of the anion concentration in the solution 12.

The voltages $E_g$ and $E_s$ are applied to a differential amplifier 16 which is arranged to produce in its output 17 an error signal voltage ($E_s - E_g = E$) representing the difference between the first and second signal voltages obtained from the cell 11. The amplifier 16 may be a conventional type having high input impedance and high common mode rejection. Preferably, the amplifier 16 is an amplifier with dual inputs and outputs having positive and negative inputs 18 and 19 receiving the first and second signal voltages $E_g$ and $E_s$, respectively. The amplifier 16 has positive output 17 and negative output 21 providing the error signal voltage E. The amplifier 16 can have a component gain of 40,000 or greater, but preferably the components of the circuit associated with this amplifier adjust the input-output circuit gain to approximately unity. This gain arrangement of the amplifier 16 with input circuitry has an exceedingly high loop impedance, stability and a high common mode of rejection. The amplifier 16 has the usual connections for receiving power and circuit common (CM) which connections have been omitted for simplifying the present description.

The output E of the amplifier 16 is applied to a reversing switch 20. The reversing switch 20 is set to the normal position when the value of E is chaning in the positive direction during titration near the end point; the reverse position when the value of E is changing in the negative direction during titration near the end point. The output E of the amplifier 16 is applied to a comparator 22 into input 23 and 24 in either the positive or negative sense depending on the position of the normal-reversing switch 20 together with a rate controlling voltage $E_o$ at the negative input 23, and there is produced a sensor signal voltage $\pm E - E_o$ at the positive output 26.

The rate controlling voltage $E_o$ may be taken from a power source represented by terminals B+ and B− through a variable resistor 28. The rate controlling voltage $E_o$ is obtained through adjustment of the resistance 28 so that a certain voltage magnitude is applied to the input 23 of the comparator 22. The forthcoming description will make clear how this certain value of the reference voltage is selected. This certain magnitude of rate controlling voltage produces the desired end point for electrochemical analysis and proper operation of the present coulometric titrator.

The comparator 22 can be of any circuitry performing the defined function $E - E_o$ and amplifiers with dual inputs-outputs arrangement adjusted for unity circuit gain can be employed to good result. The comparator 22 has the usual connections to a source of power and circuit common (CM) which are omitted for simplicity of description. The output 26 of the comparator 22 carries the sensor signal voltage $E - E_o$ to an antilogarithm converter 31.

The anti-logarithm converter 31 receives the sensor signal voltage $E - E_o$ and a referencing current $i_o$ and performs the function of producing a control signal i which is proportional to the anti-logarithm of the sensor signal voltage $E - E_o$.

The anti-logarithm converter 31 is preferably an operational amplifier particularly arranged by circuit components in an anti-logarithmic function amplifier. The amplifier employs a semiconductor junction which produces an exponential current-voltage relationship. Although there are a number of commercial devices suitable for employment as the antilogarithm converter 31, it is preferred to employ the IC module available commercially as the Intersil 8049 which may be purchased from Intersil, Inc.

The anti-logarithm converter 31 receives the sensor signal voltage $E - E_o$ at an input 32 and a referencing current $i_o$ at its other input 33, which current sets the dynamic range in the operation of the anti-logarithm conversion. The anti-logarithm converter 31 functions to produce an output signal (current) $i$ that is a function of the anti-logarithm of the sensor signal voltage $E - E_o$. The output 34 of the anti-logarithm converter 31 is a current i applied to the cell 11. The slope of the anti-logarithm function, plotted on semi-logarithmic paper, depends upon the value of D given in the equation shown in FIG. 1. The anti-logarithm converter 31 can receive a slope adjustment from the variable resistor 36 at the slope adjustment input 35. This slope adjustment can be either in the form of discrete values of resistance which are switched in or by a continuously variable potentiometer. An alternate approach and the preferred way of changing the slope of the antilog amplifier 31 is to change the gain of the comparator 22 of the preceding stage at input 37. This gain adjustment likewise can be either in the form of discrete values of resistance which are switched in or by a continuously variable potentiometer.

The output signal current i has a magnitude which is coulometrically proportional to the rate of addition of the reactive ion into the sample solution. The current flow from the output 34 of the anti-logarithm converter 31 is passed into the cell 11 through any suitable means for monitoring the total accumulation of current. Preferably, a coulometer 52 is inserted between the output 34 of the anti-logarithm converter 31 and a source of reactive ions contained in the cell 11. The coulometer 52 can be of conventional form and provides a readout indicating the total coulombs which have been passed into the cell 11. This readout may be displayed upon a suitable meter 53 calibrated in current-time increments such as milliampere seconds.

The output signal current $i$ from the coulometer 52 passes to a reactive ion source 54 contained in the cell 11 which may be either the anode or cathode. The reactive ion source is usually a metal from which current flow releases metal ions into the solution 12. For example, in a chloride ion analysis the reactive ion is the silver ion introduced into the solution 12. Thus, the reactive ion source 54 will be the anode and is a relatively pure electrode formed of metallic silver. The flow of the output signal current $i$ from the antilogarithm converter 31 produces quantitatively the introduction of the reactive ion into the solution 12 in accordance with Faraday's Law. As a result, sensor signal voltage $E - E_o$ applied to the anti-logarithm converter 31 results directly in output signal current flow $i$ for the quantitative rate of introduction of the reactive ion into the solution 12. The current $i$ returns from the solution 12 through the cathode formed by an inert electrode 56 to output 48 of the anti-logarithm converter 31. The inert electrode 56 forms the cathode for the cell 11 and the reactive ion source 54 serves as the anode for the current flow i from the anti-logarithm converter 31 in this example. In other instances, the anode can be inert and the cathode forms the reactive ions source.

The magnitude of the rate control voltage $E_o$ applied at input 23 to the comparator 22 is adjusted in the following manner. The sensor signal voltage $E - E_o$ provided in the output 26 of the comparator 22 reflects the proper adjustment of the rate control voltage $E_o$ when $E - E_o$ changes at an initial constant rate with time between $E_1$ and $E_2$ representing the end point. Stated in another manner, as the sensor signal voltage $E_s$ changes with time, it will have an initial constant slope $\Delta E$ between $E_1$ and $E_2$ which may be visualized in reference to FIG. 2. Assume that the sensor signal voltage $E_s$ begins at the error signal $E_1$ and progresses at a uniform rate between times $t_1$ and $t_2$. For a given electrochemical analysis, the rate control voltage $E_o$ will be preset to a certain value, e.g., 1.52 volts, to produce a selected $\Delta E$, e.g., 30 millivolts per minute. This desired constant rate of change of the sensor signal voltage with time can be detected by employing a differentiator 57 which has a positive input 58 connected to the output 17 of the amplifier 16. The negative input 59 of the differentiator 57 is returned to circuit common (CM). The differentiator 57 is a suitable type of operational amplifier which produces an output voltage substantially in proportion to the rate of change of the input voltage with time. The output voltage of the differentiator 57 is displayed on a readout device 61 which may be calibrated in a volt-time function such as millivolts/minute. Using the differentiator 57, the rate control voltage $E_o$ is adjusted by employing the variable resistor 28 until the desired constant rate of change is indicated on the readout device 61 for the certain rate control voltage $E_o$. It has been found with practical embodiments of the present coulometric titrator that the sensor signal voltage $E - E_o$ will change with time between 10 and 60 millivolts per minute for most electrochemical analysis. However, good results have been obtained with the sensor signal voltage $E - E_o$ changing with time at a rate of about 30 millivolts per minute. This rate of 30 millivolts/minute is especially useful where the coulometric titrator is determining the amount of chloride ion within the solution 12 using a silver metal electrode as the reactive ion source 54.

In the case of one electron ($n=1$) reactions, such as that involving the chloride ion, the constant D in the equation, $i = i_o$ antilog $[-D(E-E_o)]$, is preferably chosen as 0.059 which equals the constant in the Nernst equation for a one electron reaction. This constant controls the slope or rate of application of generating current. With reactions involving 2 ($n=2$) and 3 ($n=3$) electrons, the 0.059 slope provides an impractically low titration rate. Also in cases where the change in potential at the equivalence point is extremely small, a low titration rate is observed. Accordingly, steeper slopes corresponding to a slope of 0.029 for $n=2$ and 0.020 for $n=3$ are preferably employed for 2 and 3 electron reactions, respectively. These slopes equal the constants in the Nernst equation for such reactions.

The reactive ion is thus introduced into solution at a rate which is proportional to the demand for the reactive ion. While the demand for the reactive ion is predominately from the specific ion being titrated at some distance from the stoichiometric end point, the resulting rate of change of sensor voltage will be constant. Near the stoichiometric end point, the demand for free silver in solution starts to manifest itself. At the stoichiometric end point, the demand by said specific ion and the demand for free silver become equal resulting in a sensor electrode voltage rate of change of one-half. Once past the end point, the free silver demand becomes so large with respect to available silver addition that the sensor electrode rate of change will have dropped to a tenth with only a 28 millivolt movement past the end point and the titration for all practical purposes will have been stopped.

Because the instrument has been designed to track only the demand for silver by said specific ion, the titration comes to a halt a small distance past the end point because the demand for free silver in solution becomes predominate and soaks up what little silver generating capability is left and the titration of said specific ion has stopped. A coulometer in the silver generating loop records the number of coulombs that has passed which is a direct measure of the amount of chloride that has been titrated.

It is important to note that changing the reference voltage mentioned earlier will change the rate of change of the sensor voltage but will not change the coulometer reading. This relatively insensitive response to the reference voltage or any other shift in sensor voltage allows this instrumental technique to stand aside from all other known instrumental techniques.

The improved coulometric titrator of the present invention may be operated in the same manner as described in the specific embodiment set forth in said Wilson Application, incorporated herein by reference thereto, with an appropriate adjustment of the constant D, as hereinbefore explained. The present coulometer, of course, retains the advantages of that of Wilson, as explained in his Application, and its functioning can be better understood by referring to the mathematical explanations contained in said Wilson Application, said explanations also being incorporated herein by reference thereto.

As to this present invention, the following is a mathematical development for the silver system with an insoluble precipitate with either 1, 2 or 3 electron reactions. The mathematical development will show the apparatus conditions required to obtain a nearly constant rate of change of cell potential in the vicinity of the end point. There are four basic equations required to explain the mathematical behavior of the instrument and the silver precipitate chemical systems. Equation 1 is the modified time dependent Nernst equation:

$$E(t) = E_E - K_1 ln\, [A(t)]$$

Where
$E(t)$ is error signal voltage and a function of time
$E_E$ is the Standard Potential
$K_1$ is Constant Equal to $RT/n_rF$
R is Gas Constant
T is Absolute Temperature $n_r$ is Number of Electrons In Reaction F is Faraday's Constant $[A^{-n_r}t]$ is Ratio of Molar Solubility per unit volume of the reduced to oxidized species with oxidized value defined as 1 and a function of time.

$[A^{-n_r}]$ is the Molar solubility of said species and a function of time.

Equation 2 is the titration current sensed voltage machine relationship:

$$I(t) = I_o \text{ antilog } [-D(E(t) - E_o)]$$

Where $I(t)$ is current flowing in cell $I_o$ is current constant of titrator $D$ is constant of titrator slope $E_o$ is rate control voltage Equation 3 is the relationship between the concentration of the silver and the other specie near the equivalence point.

$$[n_r Ag^+]^{n_r} [A^{-n_r}] = K_{sp}$$

Where $[Ag^+]$ is the molar solubility of silver and a function of time.

Equation 4 is the relationship between current flow at the electrode and the change in concentration of the species in the cell, $$I(t) = n_r V K_2 \left( \frac{d[Ag^+]}{dt} - \frac{d[A^{-n_r}]}{dt} \right)$$

Where

V is the volume of the cell $K_2$ is a conversion constant $d[Ag^+]/dt$ is the time rate of change of the silver molar solubility.

$d[A^{-n_r}]/dt$ is the time rate of change of the other species' molar solubility.

These four equations can be combined to give the desired results as follows:

a. Equation 1 can become 1a.

Equation 1a $[A^{-n_r}t] = e^{-(E(t)-E_E)/K_1}$ b. Equation 1 can be differentiated with respect to time to give equation 5.

Equation 5:

$$\frac{dE(t)}{dt} = -K_1/[A^{-n_r}t] \times \frac{d[A^{-n_r}]}{dt}$$

c. Equation 1a can be substituted into equation 5 to give equation 6.

Equation 6:

$$\frac{dE(t)}{dt} = \frac{-K_1}{e^{-(E(t)-E_E)/K_1}} \times \frac{d[A^{-n_r}]}{dt}$$

d. Equation 3 can be substituted into equation 4 to give equation 7.

Equation 7:

$$I(t) = n_r V K_2 \left[ \frac{K_{sp}^{1/n_r}}{n_r} \frac{d[A^{-n_r}]^{-1/n_r}}{dt} - \frac{d[A^{-n_r}]}{dt} \right]$$

e. Equation 7 can be rewritten as equation 7a.

Equation 7a:

$$I(t) = -n_r V K_2 \left[ \frac{K_{sp}^{1/n_r}}{n_r^2 [A^{-n_r}] (1/n_r + 1)} + 1 \right] \frac{d[A^{-n_r}]}{dt}$$

f. Equation 7a can be substituted into equation 6 to give equation 8.

Equation 8:

$$\frac{dE(t)}{dt} = \frac{K_1 I(t)}{n_r V K_2 e^{-(E(t)-E_E)/K_1} \left\{ 1 + \frac{K_{sp}^{1/n_r}}{n_r^2 [A^{-n_r}] (1/n_r + 1)} \right\}}$$

g. Equation 2 can be substituted into equation 8 to give equation 9.

Equation 9:

$$\frac{dE(t)}{dt} = \frac{K_1 I_o e^{[E(t)(1/K_1 - D) + DE_o - \frac{E_E}{K_1}]}}{n_r V K_2 \left\{ 1 + \frac{K_{sp}^{1/n_r}}{n_r^2 [A^{-n_r}] (1/n_r + 1)} \right\}}$$

If $D = 1/K_1$ then $dE(t)/dt$ is independent of $E(t)$ and is nearly constant. At equivalence $K_{sp} = n_r^{n_r} [A^{-n_r}]^{(n_r + 1)}$. This can be substituted into equation 9 to give the value of $dE(t)/dt$ at equivalence. The value changes a factor of only ½ from large concentration of $[A^{+n_r}]$ to the equivalence point in a slowly varying manner for $n_r=1$; a factor of ⅔ for $n_r=2$; and a factor of ¾ for $n_r=3$.

h. Equation 9a:

$$\frac{dE(t)}{dt} = \frac{K_1 I_o e^{[E(t)(1/K_1 - D) + DE_o - \frac{E_E}{K_1}]}}{n_r V K_2 \left( 1 + \frac{1}{n_r} \right)}$$

The condition $D=1/K_1$ means that slope of the antilog function in the titrator must be equal to $n_r F/RT$ or the slope is directly proportioned to the number of electrons involved in the reaction. For the condition $D = 1/K_1$ equation 9 becomes i. Equation 9b:

$$\frac{dE(t)}{dt} = \frac{K_1 I_o e^{\frac{n_r F}{RT}(E_o - E_E)}}{n_r V K_2 \left( 1 + \frac{K_{sp}^{1/n_r}}{n_r^2 [A^{-n_r}] (n_r + 1)/n_r} \right)}$$

Figure 2:
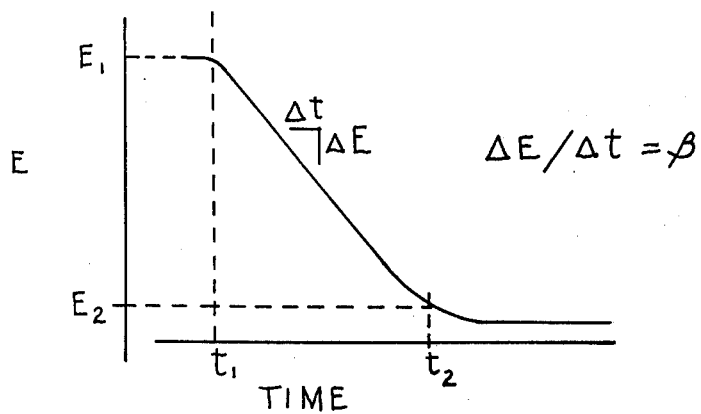
FIG. 2 is a graph illustrating the linear sensor signal voltage change with time to the comparator means for a properly selected reference voltage.
Figure 3:
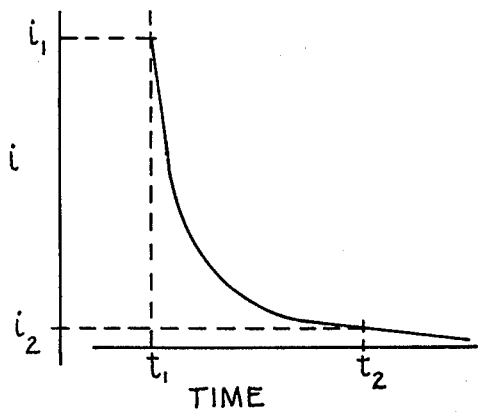
FIG. 3 is a graph illustrating the current flow to the reactive ion source means with the proper reference voltage making the sensor signal voltage change with time in a linear relationship.

FIG. 3 shows the current response of the titrator as a function of time when the voltage response is as shown in FIG. 2. The current starts at a high level to allow for rapid completion of the titration, then decreases to a lower level to allow the titration to go to completion without over-shoot.

Figure 4:
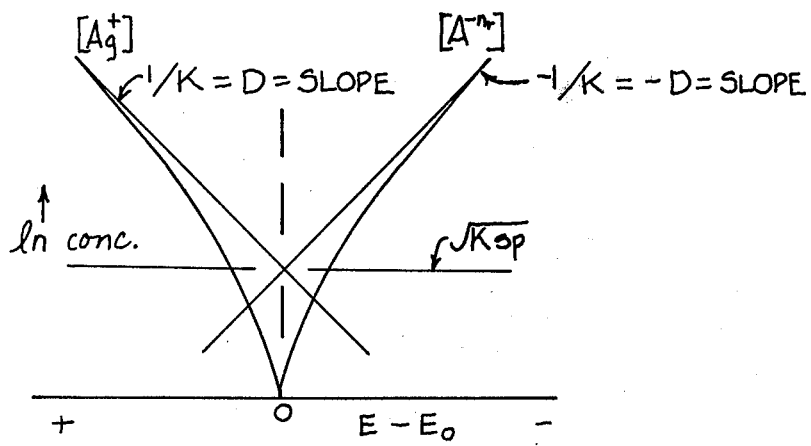
FIG. 4 is a graph illustrating the Tafel slope curves and solubility product, relative to sensor electrode voltages in a sample solution.

FIG. 4 shows the relationship between the concentrations of the species in cell 11 of FIG. 1, and the sensor signal voltage $E - E_o$ when the rate controlling voltage $E_o$ is set to the equivalence point value. This figure is a graphical representation of the Nernst type relationship.

The present coulometric titrator is applicable to various studies in electrochemical analysis, and it is not limited merely to the described potentiometric precipitation titrations. Other uses for the coulometric titrator include: potentiometric oxidation-reduction titrations, determinations of ionization constant and solubility product constant, and coulometric electrolysis wherein the working electrode potential control will be automatically obtained. Moreover, the instrument can be used in another mode as an end point titrator in quickly responding chemical systems. In this mode, a slope higher than $n = 1, 2$ or $3$ is used, and the titrator runs in a constant current manner because the current generation capacity is limited. As the instrument approaches the value of $E_o$, set by the operator, the logarithmic current relation occurs depending on the slope selected and slows down the current flow as the titration is completed. Slopes of values as high as $n = 12$ can be used.

Various modifications and alterations which do not depart from the spirit of the invention in the described coulometric titrator will be apparent to those skilled in the art from the foregoing description. For this reason, these changes in elements and functioning are desired to be included within the scope of the present invention. The appended claims define the present invention and the foregoing description is to be employed for setting forth these specific embodiments as illustrative in nature.

We claim:

1. A coulometric titrator for determining the amount of a specific ion in a sample solution by the reaction with a reactive ion comprising:
   (a) a cell for containing said sample solution and including electrodes for immersion in said solution, said electrodes including a reference electrode providing a first signal voltage and a specific ion sensing electrode providing a second signal voltage representing the logarithm of the concentration of the specific ion in said sample solution;
   (b) differential input amplifier means having as inputs said first and second signal voltages from said reference and specific ion sensing electrodes and said differential input amplifier having as its output an error signal voltage representing the difference between said first and second signal voltages;
   (c) reversing switch means receiving as input said error signal voltage and providing as output said error signal voltage in either the positive or negative sense depending on the position of said switch;
   (d) reference means providing a reference voltage for the specific ion in the solution indicative of a particular rate of change of the second signal voltage while said rate of change of the second signal voltage is constant;
   (e) comparator means receiving as inputs the signal voltage from said reversing switch and said reference voltage and providing as its output a sensor signal voltage representing the difference between said error signal and reference voltages;
   (f) antilogarithm converter means receiving said sensor signal voltage and having an output signal that is a function of the antilogarithm of said sensor signal voltage, said function being represented by the equation:

$$i = i_o \text{antilog} [[-D(E-E_o)]] (-D(E-E_o)),$$

where
   $i$ = output signal current
   $i_o$ = referencing current
   $E - E_o$ = sensor signal voltage
   $D$ = slope of the function plotted on semi-logarithmic paper;
   (g) means for adjusting said slope $D$, said means adapted to give slopes ranging from 0.020 to 0.059; and
   (h) reactive ion source means in the sample solution receiving said output signal and associated with a current source providing an unidirectional current flow between an anode and a cathode immersed in the sample solution and said reactive ion source means is either the anode or the cathode with the other being inert and with the quantum rate of reactive ion introduction into the sample solution being proportional to said output signal, whereby said second signal voltage changes at a constant rate with time and said reactive ion addition changes in a logarithmically decreasing amount with time in the sample solution until the stoichiometric end point is approached.

2. The coulometric titrator of claim 1 wherein a differentiator means receives as its input said error signal voltage and provides as an output a readout signal representing the change in the second signal voltage with time.

3. The coulometric titrator of claim 2 wherein said readout signal represents a change in sensor signal voltage with time between 10 and 60 millivolts per minute.

4. The coulometric titrator of claim 1 wherein a coulometer means monitors said current flow from said current source and provides a readout of the total coulomb amount.

5. The coulometric titrator of claim 1 wherein said slope adjustment means comprises a variable resistance means which provides an input to said antilogarithm converter.

6. The coulometric titrator of claim 1 wherein said slope adjustment means comprises means for changing the gain of said comparator means.

7. The coulometric titrator of claim 1 wherein said reactive ion source means is the anode.

8. A coulometric titrator for determining the amount of a specific ion in a sample solution by the reaction with a reactive ion comprising:
   (a) a cell for containing said sample solution and including electrodes for immersion in said solution, said electrodes including a reference electrode providing a first signal voltage and a specific ion sensing electrode providing a second signal voltage representing the logarithm of the concentration of the specific ion in said sample solution;
   (b) differential input amplifier means having as inputs said first and second signal voltages from said reference and specific ion sensing electrodes and said differential input amplifier having as its output an error signal voltage representing the difference between said first and second signal voltages;
   (c) reversing switch means receiving as input said error signal voltage and providing as output said error signal voltage in either the positive or negative sense depending on the position of said switch;
   (d) reference means providing a reference voltage for the specific ion in the solution indicative of a particular rate of change of the second signal voltage while said rate of change of the second signal voltage is constant;
(e) comparator means receiving as inputs the signal voltage from said reversing switch and said reference voltage and providing as its output a sensor signal voltage representing the difference between said error signal and reference voltages;
(f) antilogarithm converter means receiving said sensor signal voltage and having an output signal that is a function of the antilogarithm of said sensor signal voltage; and
(g) reactive ion source means in the sample solution receiving said output signal and associated with a current source providing an unidirectional current flow between an anode and a cathode immersed in the sample solution and said reactive ion source means is either the anode or the cathode with the other being inert and with the quantum rate of reactive ion introduction into the sample solution being proportional to said output signal, whereby said second signal voltage changes at a constant rate with time and said reactive ion addition changes in a logarithmically decreasing amount with time in the sample solution until the stoichiometric end point is approached.

9. A coulometric titrator for determining the amount of a specific ion in a sample solution by the reaction with a reactive ion comprising:
(a) a cell for containing said sample solution and including electrodes for immersion in said solution, said electrodes including a reference electrode providing a first signal voltage and a specific ion sensing electrode providing a second signal voltage representing the logarithm of the concentration of the specific ion in said sample solution;
(b) differential input amplifier means having as inputs said first and second signal voltages from said reference and specific ion sensing electrodes and said differential input amplifier having as its output an error signal voltage representing the difference between said first and second signal voltages;
(c) reference means providing a reference voltage for the specific ion in the solution indicative of a particular rate of change of the second signal voltage while said rate of change of the second signal voltage is constant;
(d) comparator means receiving as inputs said error signal voltage and said reference voltage and providing as its output a sensor signal voltage representing the difference between said error signal and reference voltages;
(e) antilogarithm converter means receiving said sensor signal voltage and having an output signal that is a function of the antilogarithm of said sensor signal voltage, said function being represented by the equation:

$$i = i_o \text{ antilog } [[-D(E-E_o)]](-d(E-E_o)),$$

where
$i$ = output signal current
$i_o$ = referencing current
$E-E_o$ = sensor signal voltage
$D$ = slope of the function plotted on semi-logarithmic paper;
(f) means for adjusting said slope $D$, said means adapted to give slopes ranging from 0.020 to 0.059; and
(g) reactive ion source means in the sample solution receiving said output signal and associated with a current source providing an unidirectional current flow between an anode and a cathode immersed in the sample solution and said reactive ion source means is either the anode or the cathode with the other being inert with the quantum rate of reactive ion introduction into the sample solution being proportional to said output signal, whereby said second signal voltage changes at a constant rate with time and said reactive ion addition changes in a logarithmically decreasing amount with time in the sample solution until the stoichiometric end point is approached.

* * * * *